(12) United States Patent
Braude et al.

(10) Patent No.: US 7,618,976 B2
(45) Date of Patent: Nov. 17, 2009

(54) METHODS FOR THE PRODUCTION OF SILDENAFIL BASE AND CITRATE SALT

(75) Inventors: Viviana Braude, Kadima (IL); Judith Aronhime, Rehovot (IL); Shalom Shabat, Yavne (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 275 days.

(21) Appl. No.: 11/030,545

(22) Filed: Jan. 5, 2005

(65) Prior Publication Data

US 2005/0182066 A1 Aug. 18, 2005

Related U.S. Application Data

(60) Provisional application No. 60/534,527, filed on Jan. 5, 2004, provisional application No. 60/547,232, filed on Feb. 23, 2004, provisional application No. 60/549,268, filed on Mar. 1, 2004.

(51) Int. Cl.
  *C07D 487/04* (2006.01)
  *A61K 31/519* (2006.01)
(52) U.S. Cl. .................... 514/262.1; 544/262
(58) Field of Classification Search ............. 544/262; 514/262.1
   See application file for complete search history.

(56) References Cited

U.S. PATENT DOCUMENTS

| | | | |
|---|---|---|---|
| 4,151,273 A | 4/1979 | Riegelman et al. | |
| 4,196,188 A | 4/1980 | Besins | |
| 4,302,446 A | 11/1981 | Kaplan et al. | |
| 4,840,799 A | 6/1989 | Appelgren et al. | |
| 5,250,534 A * | 10/1993 | Bell et al. ............ | 514/252.16 |
| 5,271,944 A | 12/1993 | Lee | |
| 7,005,520 B2 | 2/2006 | Dunn et al. | |
| 7,067,660 B2 | 6/2006 | Bunnage et al. | |
| 2002/0013464 A1 | 1/2002 | Dunn et al. | |

FOREIGN PATENT DOCUMENTS

| | | |
|---|---|---|
| EP | 0 463 756 A1 | 1/1992 |
| EP | 0 812 845 A1 | 12/1997 |
| WO | WO 98/49166 A1 | 11/1998 |
| WO | WO 01/87888 * | 11/2001 |
| WO | WO 02/102802 A1 | 12/2002 |
| WO | WO 2004/072079 A1 | 8/2004 |
| WO | WO 2005/013937 | 2/2005 |

OTHER PUBLICATIONS

Third party observation concerning EP Application No. 07101908.7 / EP 1779852 as filed by the law firm Hoffmann Eitle with EPO on Aug. 20, 2008.
Admour, I.M. et al., "Solid Modifactions in Sildenafil Citrate," World Meeting APV/APGI, Apr. 3, 2000, pp. 639-640.
Dunn, P.J., "Synthesis of Commercial Phosphodiesterase(V) Inhibitors," Organic Process Research and Development, (2005) vol. 9(1) pp. 88-97, Cambridge, GB.
Shenyang Yaoke Daxue Xuebao-Shenyang Pharmaceutical University Journal, May 2002, vol. 19(3), pp. 173-175, (Chinese Only).
International Search Report of PCT/US05/000207 mailed Sep. 23, 2005.

* cited by examiner

*Primary Examiner*—Bruck Kifle
(74) *Attorney, Agent, or Firm*—Kenyon & Kenyon LLP

(57) ABSTRACT

Provided are processes for the preparation of sildenafil base and the citrate salt of sildenafil. Also provided are sildenafil citrate water adduct and a method of preparing pharmaceutical compositions comprising combining the sildenafil citrate and/or sildenafil citrate water adduct with at least one pharmaceutically-acceptable excipient.

28 Claims, No Drawings

METHODS FOR THE PRODUCTION OF SILDENAFIL BASE AND CITRATE SALT

CROSS-REFERENCE TO RELATED APPLICATIONS

This application claims the benefit of U.S. Provisional Application Nos. 60/534,527 filed on Jan. 5, 2004, 60/547,232 filed on Feb. 23, 2004 and 60/549,268 filed on Mar. 1, 2004, the disclosures of which are incorporated by reference in their entirety herein.

FIELD OF THE INVENTION

The invention encompasses processes for the preparation of sildenafil and the citrate salt of sildenafil. The invention also encompasses sildenafil citrate water adduct and a method of preparing pharmaceutical compositions comprising combining the sildenafil citrate and/or sildenafil citrate water adduct with at least one pharmaceutically-acceptable excipient.

BACKGROUND OF THE INVENTION

Sildenafil citrate is a selective inhibitor of cyclic guanosine monophosphate (cGMP)-specific phophodiesterase type 5 (PDE5), commercially developed by Pfizer, Inc. as VIAGRA®. Sildenafil citrate is designated chemically as 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine citrate, having a molecular weight of 666.7, and the following chemical structure:

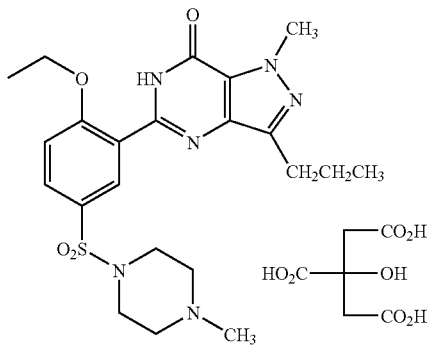

Sildenafil citrate is a white to off-white crystalline powder with a solubility of 3.5 mg/ml in water. The physiologic mechanism of erection of the penis involves release of nitric oxide (NO) in the corpus cavernosum during sexual stimulation. NO then activates the enzyme guanylate cyclase, which results in increased levels of cyclic guanosine monophosphate (cGMP), producing smooth muscle relaxation in the corpus cavernosum and allowing the inflow of blood. Sildenafil has no direct relaxant effect on isolated human corpus cavernosum, but enhances the effect of nitric oxide by inhibiting phosphodiesterase type 5, which is responsible for degradation of cGMP in the corpus cavernosum. When sexual stimulation causes local release of NO, inhibition of PDE5 by sildenafil causes increased levels of cGMP in the corpus cavernosum, resulting in smooth muscle relaxation and inflow of blood to the corpus cavernosum. Sildenafil at recommended doses has no effect in the absence of sexual stimulation.

The synthesis of pyrazolopyrimidinone compounds was described as the reaction of a chlorosulfonyl compound with a cyclic amine. As the reaction progresses, however, mineral acids are produced which may further react with the product or starting materials thereby reducing the overall yield. For example, U.S. Pat. No. 5,250,534 to Bell et al. generically describes the synthesis of various pyrazolopyrimidinone compounds. A sulfonyl chloride is allowed to react with an excess of cyclic amine at room temperature to yield the desired product. The process, however, uses an excess of the cyclic amine, which can be economically prohibitive depending on the cyclic amine used. Additionally, because the protonated amine compound is similar to the final product, purification is complicated by the difficulty in removing the side-product from the reaction mixture.

The invention is directed to processes for synthesizing sildenafil citrate which reduce the undesired side-products commonly associated with known methods in the art. The present also provides soluble or easily dissolved sildenafil citrate water adduct for use in pharmaceutical compositions.

SUMMARY OF THE INVENTION

The invention encompasses processes for synthesizing sildenafil base and sildenafil citrate. In particular, the invention encompasses methods of preparing sildenafil and sildenafil citrate using organic solvents and environmentally friendly reaction conditions, thereby reducing waste products which are difficult to dispose of and increase manufacture costs. The invention further encompasses sildenafil citrate water adduct and a method of preparing pharmaceutical compositions using the same.

In one embodiment, the invention encompasses a process for synthesizing sildenafil comprising combining 3-(4,7-dihydro-1-methyl-7-oxo-3-propyl-1H-pyrazolo(4,3-d)pyrimidin-5-yl)-(4-ethoxyphenyl)benzene sulfonyl chloride with at most about 1 molar equivalent of N-methyl piperazine, at least one organic solvent, and at least one proton scavenger into a reaction mixture to form sildenafil. The proton scavenger may be an organic or inorganic base.

In another embodiment, the process for preparing sildenafil comprises combining 3-(4,7-dihydro-1-methyl-7-oxo-3-propyl-1H-pyrazolo(4,3-d)pyrimidin-5-yl)-(4-ethoxyphenyl)benzene sulfonyl chloride with N-methyl piperazine, at least one organic solvent, and at least one inorganic proton scavenger into a reaction mixture to form sildenafil.

The invention further encompasses synthesizing the citrate salt of sildenafil comprising combining citric acid with sildenafil base. Optionally, the sildenafil may be isolated and/or purified prior to proceeding to synthesis of sildenafil citrate.

The invention further encompasses sildenafil citrate water adduct comprising water in the amount of from about 0.3% to about 2% by weight, preferably from about 1.5% to about 1.7% by weight, wherein the sildenafil citrate water adduct has a particle size of less than about 100 microns.

One embodiment of the invention encompasses sildenafil citrate water adduct comprising water in the amount of from about 0.3% to about 2% by weight, preferably from about 1.5% to about 1.7% by weight, wherein the sildenafil citrate water adduct particles have a surface area of from about 4 $m^2/g$ to about 6 $m^2/g$.

Another embodiment of the invention encompasses sildenafil citrate water adduct comprising water in the amount of from about 0.3% to about 2% by weight, preferably from about 1.5% to about 1.7% by weight, and a melting point in the range of from about 185° C. to about 193° C.

Yet another embodiment of the invention encompasses sildenafil citrate having a melting point in the range of from about 185° C. to about 190° C.

The invention also encompasses a method of preparing pharmaceutical compositions comprising combining the sildenafil citrate water adduct of the invention with at least one pharmaceutically-acceptable excipient.

DETAILED DESCRIPTION OF THE INVENTION

The terms "sildenafil base" and "sildenafil" are used interchangeably herein.

The invention encompasses methods of preparing sildenafil base and sildenafil citrate in high yield with little or no purification required. The processes of the invention allow for economical synthesis, shorter reaction times, and higher yields. In addition, the synthesis of sildenafil citrate may be carried out in a one pot synthetic scheme, i.e., sildenafil is prepared and subsequently sildenafil citrate salt is prepared without changing reaction vessels.

In one embodiment, the invention encompasses synthesizing sildenafil comprising combining 3-(4,7-dihydro-1-methyl-7-oxo-3-propyl-1H-pyrazolo(4,3-d)pyrimidin-5-yl)-(4-ethoxyphenyl)benzene sulfonyl chloride with at most about 1 molar equivalent of N-methyl piperazine, at least one organic solvent, and at least one proton scavenger into a reaction mixture to form sildenafil. Preferably, the N-methyl piperazine is present in an amount of about 1 molar equivalent of the benzene sulfonyl chloride.

In another embodiment, the process for synthesizing sildenafil comprises combining 3-(4,7-dihydro-1-methyl-7-oxo-3-propyl-1H-pyrazolo(4,3-d)pyrimidin-5-yl)-(4-ethoxyphenyl)benzene sulfonyl chloride with N-methyl piperazine, at least one organic solvent, and at least one inorganic proton scavenger into a reaction mixture to form sildenafil. The N-methyl piperazine used in this process can be present in any amount sufficient for the reaction to proceed. The N-methyl piperazine can be in excess of the benzene sulfonyl chloride, or it can be present in an amount of at most about 1 mol of N-methyl piperazine per mole of the benzene sulfonyl chloride.

When preparing the reaction mixture, the order by which the N-methyl piperazine, proton scavenger, and sulfonyl chloride are added should be taken into consideration. If addition of the N-methyl piperazine or proton scavenger is delayed after sulfonyl chloride is added to the mixture, potential hydrolysis of the chlorosulfonyl derivative to its corresponding acid may result in a poor impurity profile. In a preferred embodiment, the benzene sulfonyl chloride is added to the reaction mixture after the N-methyl piperazine and proton scavenger are added. Example 34 illustrates one preferred embodiment. The benzene sulfonyl chloride may be added all at once, or in separate portions. The benzene sulfonyl chloride can also be added as a solid in addition to acetone slurry form.

Suitable organic solvents for the synthesis of sildenafil include, but are not limited to, at least one of acetone, isopropanol, ethanol, methanol, acetonitrile, ethyl acetate, methyl ethyl ketone, dichloromethane, or toluene. Preferably, the organic solvent is at least one of acetone, ethanol, or methanol. Sufficient organic solvent should be added to allow the reaction to proceed, for example, the solvent should be added in an amount of about 5 ml to about 40 ml per gram of sildenafil. Optionally, water may be added to the reaction mixture. If added, water is preferably present in a ratio of about 1:2 water to organic solvent by volume.

The reaction temperature should be sufficient to effect condensation. Typically, the reaction temperature may be from about 0° C. to about reflux temperature. Preferably, the reaction temperature is about room temperature (25° C.) to about 40° C.

The proton scavenger can be any compound that reacts with protons in solution in a manner to remove the protons from reacting with other chemicals or compounds within the reaction mixture. The proton scavenger can be an organic or inorganic base. Preferred organic proton scavengers include, but are not limited to, at least one of triethylamine, dimethylaminopyridine, or di-tertbutylaniline. Preferred inorganic proton scavengers include, but are not limited to, at least one of NaOH, KOH, $NaHCO_3$, $KHCO_3$, $Na_2CO_3$, $K_2CO_3$, or $Ca(OH)_2$. The amount of proton scavenger can be from about 0.8 mol to about 1.5 mol per mol of the benzene sulfonyl chloride reagent, preferably about 1 mol per mol of the benzene sulfonyl chloride reagent.

Sildenafil may be isolated by methods commonly known in the art. Generally, the reaction mixture may be cooled to about 0° C., upon which a precipitate appears. The precipitate may then be collected to obtain the isolated product sildenafil. Optionally, sildenafil may be dried while heated and/or under vacuum. For example, sildenafil may be dried at a temperature of about 50° C. under a vacuum of about 10 mm Hg.

The invention also encompasses processes for the synthesis sildenafil citrate comprising synthesizing sildenafil followed by reaction with citric acid to synthesize sildenafil citrate. In this embodiment, sildenafil may be synthesized and immediately allowed to react with citric acid, i.e. without changing reaction vessels, or sildenafil may be synthesized and/or isolated and then allowed to react with citric acid to form sildenafil citrate. If isolated prior to the synthesis of sildenafil citrate, sildenafil may optionally be purified by any method known in the art.

The synthesis of sildenafil citrate comprises combining into a reaction mixture citric acid with sildenafil. Preferably, the citric acid is present in an amount of about 1 mol equivalent to about 2 mol equivalents of sildenafil, more preferably from about 1 mol equivalent to about 1.5 mol equivalents of sildenafil.

The reaction mixture to form sildenafil citrate may further comprise at least one organic solvent. The citric acid may be combined with the organic solvent before being added to the sildenafil, or the citric acid may be added directly into the reaction mixture comprising sildenafil and the organic solvent. Preferably, the organic solvent includes, but is not limited to, at least one of acetone, acetonitrile, methanol, ethanol, isopropanol, ethyl acetate, isobutyl acetate, butyl acetate, methyl acetate, toluene, heptane, or methylene chloride. More preferably, the organic solvent is acetone. Preferably, the organic solvent is present in an amount of about 2 to about 40 times the volume of the reagents. Optionally, water may be added to the reaction mixture to form the citrate salt. A preferred solvent-water combination is acetone and water. The organic solvent used to form sildenafil citrate can be the same as the organic solvent used in the preparation of sildenafil, or they can be different.

The reagents may be added as solids and mixed with the solvents, such as a slurry reaction. Alternatively, each reagent may be dissolved in its selected solvent, and the two solutions are then combined. For example, citric acid may be first dissolved in a solution such as acetone, and then added to the sildenafil base solution.

The preferred reaction temperature for sildenafil citrate formation is from about 0° C. to about 130° C., more preferably at about reflux temperature, for example, about 56° C.

for acetone solvent. Depending upon reaction conditions, the reaction may be immediate or can take as long as 24 hours.

The sildenafil citrate may be dried using methods commonly known to one skilled in the art. Typically, the drying methods include heat and/or vacuum. For example, sildenafil citrate may be dried by heating to a temperature of about 50° C. to about 100° C. under a vacuum of about 2 mm Hg. The time for drying may vary depending upon variables known to the skilled artisan such as product wetness, temperature, and vacuum.

The sildenafil citrate obtained by the above method may be isolated as a wet crystal or as a hydrate wherein the water content is from about 1.2% to about 1.7% as measured by Karl Fischer method.

The invention also encompasses sildenafil citrate water adduct, or sildenafil citrate complexed with water. Not to be limited by theory, it is believed that sildenafil citrate complexed with water has increased stability. The sildenafil citrate water adduct of the invention is suitable for use in pharmaceutical formulations, having advantages such as good bulk properties and good mixing properties.

Water may be present in the adduct in an amount of about 0.3% to about 2% by weight, preferably in an amount of about 0.5% to about 2% by weight of the sildenafil. More preferably, water is present in the sildenafil citrate adduct in an amount of about 1% to about 2% by weight, and most preferably, in an amount of about 1.5% to about 1.7%. Alternatively, the water content may be expressed as a molar ratio. For example, water may be present in a ratio of about 0.1 mol to about 0.8 mol of water per mole of sildenafil citrate. Preferably, the water is present in a ratio of about 0.2 mol to about 0.8 mol of water per mole of sildenafil citrate. The amount of water in sildenafil citrate is easily determined by one of ordinary skill in the art. For example, the skilled artisan can easily determine the amount of water using the standardized Karl Fisher method.

The sildenafil citrate water adduct of the invention may be milled into particles of a particular size or shape to further increase dissolution and solubility. The formation of particles in sizes disclosed herein can be obtained by methods well known in the art (See U.S. Pat. Nos. 4,151,273; 4,196,188; 4,302,446; 4,840,799; and 5,271,944). One common technique to decrease particle size is by micronization. Micronization is a mechanical process that involves the application of force to a particle, thereby resulting in the break-up of the particle. Such force may be applied by collision of particles at high speeds. Micronization may be carried out, for example, by grinding or by an air-jet micronizer.

Typically, the sildenafil citrate water adduct of the invention has a particle size of less than about 100 microns. Preferably, the particle size is less than about 50 microns, more preferably less than about 20 microns. As used herein, the term "particle size" refers to the maximum size of particles in the sample. For example, a particle size of 100 microns means that all of the sildenafil citrate water adduct particles have a size below that value. The size of a particle is determined by the particle diameter, which may be measured by any of the methods commonly known in the art. The following methods, for example, may be used: sieves, sedimentation, electrozone sensing (coulter counter), microscopy, or Low Angle Laser Light Scattering (LALLS). The preferred methods for the present invention are the methods most commonly used in the pharmaceutical industry, such as laser diffraction or sieve analysis.

The laser diffraction method used to characterize the particle size distribution of sildenafil citrate may be for instance Malvern Mastersizer S equipped with a small cell dispersion unit with a digital dispersion unit controller. The measurement may be done using lens 300RF (0.05-900 microns) and presentation 3OHD. In this case, the dilution medium used may be Silicon fluid F-10. The sample may be added as a powder into the measurement cell in small quantities. Generally, the measurement may be started after 3 minutes of recirculation at speed rate of approximately 3400±10 rpm. Following the accepted rules of Good Manufacture Procedures, the sildenafil citrate sample is preferably measured after performing a successful blank measurement (% obscuration no more than (NMT) 0.1%). Although the laser diffraction method is exemplified, any other method to determine particle size distribution accepted in the pharmaceutical industry, like other instruments of laser diffraction or sieve analysis, may be used with the provision that the result obtained is reasonably accurate, i.e., within widely accepted industrial standards.

The sildenafil citrate water adduct is useful for pharmaceutical purposes such as drug formulation. Sildenafil citrate dissolution properties may be further enhanced by providing sildenafil citrate water adduct having a high surface area. In a preferred embodiment, the sildenafil citrate water adduct has a specific surface area of about 4 $m^2/g$ to about 6 $m^2/g$, more preferably about 5 $m^2/g$.

The sildenafil citrate water adduct of the invention has a melting point in the range of about 185° C. to about 193° C. Preferably, the melting point of the water adduct is from about 188° C. to about 192° C., more preferably from about 189° C. to about 191° C. Most preferably, the melting point of the water adduct is from about 189° C. to about 190° C. The melting point may be measured using the standard method of melting point described in the USP.

Another embodiment of the invention encompasses sildenafil citrate having a melting point in the range of from about 185° C. to about 190° C.

The invention further encompasses a method of preparing pharmaceutical compositions comprising combining the sildenafil citrate and/or the sildenafil citrate water adduct of the invention with at least one pharmaceutically-acceptable excipient. Any excipient commonly known and used widely in the art, such as carriers, fillers, bulking agents, binders, wetting agents, disintegrating agents, surface active agents, lubricants, or diluents can be used in the pharmaceutical composition. For example, carriers include, but are not limited to, lactose, white sugar, sodium chloride, glucose, urea, starch, calcium carbonate, kaolin, crystalline cellulose, and silicic acid. Binders include, but are not limited to, water, ethanol, propanol, simple syrup, glucose solutions, starch solutions, gelatin solutions, carboxymethyl cellulose, shelac, methyl cellulose, potassium phosphate, and polyvinylpyrrolidone. Disintegrating agents include, but are not limited to, dried starch, sodium alginate, agar powder, laminalia powder, sodium hydrogen carbonate, calcium carbonate, fatty acid esters of polyoxyethylene sorbitan, sodium lauryl sulfate, monoglyceride of stearic acid, starch, or lactose. Disintegration inhibitors include, but are not limited to, white sugar, stearin, coconut butter, or hydrogenated oils. Absorption accelerators include, but are not limited to, quaternary ammonium base, and sodium lauryl sulfate. Wetting agents include, but are not limited to, glycerin, or starch. Adsorbing agents include, but are not limited to, starch, lactose, kaolin, bentonite, or colloidal silicic acid. Lubricants include, but are not limited to, purified talc, stearates, boric acid powder, and polyethylene glycol. Tablets can be further coated with commonly known coating materials such as sugar coated tablets, gelatin film coated tablets, tablets coated with enteric coatings, tablets coated with films, double layered tablets, or multi-layered tablets.

Various types of dosage forms can be prepared from the pharmaceutical compositions comprising the sildenafil citrate water adduct, depending on the therapeutic purpose, for example tablets, pills, powders, liquids, solutions, suspensions, emulsions, granules, capsules, injection preparations (solutions and suspensions), or the like. The preferred dosage form is a tablet, preferably a 25 mg, 50 mg, or 100 mg tablet.

When tableting the pharmaceutical composition, any commonly known excipient used in the art can be used. For example, carriers include, but are not limited to, lactose, starch, coconut butter, hardened vegetable oils, kaolin, or talc. Binders include, but are not limited to, gum arabic powder, tragacanth gum powder, gelatin, or ethanol. Disintegrating agents include, but are not limited to, agar, or laminalia.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, or fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, or analgesic agents may be added. If necessary, coloring agents, preservatives, perfumes, seasoning agents, sweetening agents, or other medicines may also be added.

Having described the invention with reference to certain preferred embodiments, other embodiments will become apparent to one skilled in the art from consideration of the specification. The invention is further described by reference to the following examples disclosing in detail the surface area measurement of the sildenafil citrate of the invention. It will be apparent to those skilled in the art that many modifications, both to materials and methods, may be practiced without departing from the scope of the invention.

EXAMPLES

Example 1

General Preparation of Sildenafil

In a 3-necked flask, 3-(4,7-dihydro-1-methyl-7-oxo-3-propyl-1H-pyrazolo(4,3-d)pyrimidin-5-yl)-(4-ethoxyphenyl)benzene sulfonyl chloride (5 g, 12.2 mmol) was mixed with acetone (100 ml) at room temperature, then aqueous NaOH 47% (0.487 g, 10 mmol) was added. N-methyl piperazine (1.34 g, 11 mmol) was added dropwise. The reaction mixture was stirred for 45 mm, then cooled to 0° C. and filtered. The precipitate was washed with water twice and dried at 50° C. under 10 mm Hg to give sildenafil in a 88.8% yield.

Examples 2-13

Using the procedure described in Example 1, the reaction solvent and proton scavenger were varied. Table 1 describes the solvent, proton scavenger, and yield.

TABLE 1

Yield of Sildenafil Synthesis using a Variety of Solvents.

| Experiment No. | Solvent System | % Yield by Weight |
|---|---|---|
| 2 | Acetone/Triethylamine | 72.7 |
| 3 | Isopropanol/Triethylamine | 86.1 |
| 4 | Acetone/NaOH$_{aq}$ | 57.5 |
| 5 | Acetone/Triethylamine | 62.3 |
| 6 | Isopropanol/Triethylamine | 95.5 |
| 7 | Ethyl Acetate/NaOH$_{aq}$ | 76.5 |
| 8 | Ethanol/Triethylamine | 67.1 |
| 9 | Methyl ethyl ketone/Triethylamine | 72 |
| 10 | Methanol/Triethylamine | 91 |
| 11 | Toluene/NaOH$_{aq}$ | 75.7 |
| 12 | Methanol-Water/NaOH | 70 |
| 13 | Acetonitrile/Triethylamine | 73 |

Example 14

Synthesis of Sildenafil Citrate

In a 3-necked flask sildenafil (5 g, 10 mmol) was dissolved in acetone (40 ml) at 50° C. In a separate container, citric acid (2 g, 10 mmol) was dissolved in acetone (15 ml). Both solutions were filtered. The citric acid solution was added dropwise to the sildenafil solution and a white precipitate appeared immediately. Thereafter, the reaction mixture was heated and maintained at the solvent reflux temperature for 1 hour and subsequently allowed to cool over 3 hours to room temperature. The precipitate was collected by filtration and dried at 50° C. under 10 mm Hg to give sildenafil citrate in 95.5% yield.

Example 15-23

Using the procedure described in Example 14, the reaction solvent was varied. Table 2 describes the solvent and yield.

TABLE 2

Yield of Sildenafil Citrate using a Variety of Solvents

| Experiment No. | Solvent System | % Yield by Weight |
|---|---|---|
| 15 | Acetone | 92.6 |
| 16 | Acetone/Water | 71.2 |
| 17 | Isopropanol | 85 |
| 18 | Methanol | 81.9 |
| 19 | Ethanol | 96.2 |
| 20 | Ethyl Acetate | 85.5 |
| 21 | Toluene/Methanol | 99.7 |
| 22 | Isopropanol/Water | 74.8 |
| 23 | Ethanol/Heptane | 81.9 |

Example 24

Preparation of Sildenafil

In a 3-necked flask, 3-(4,7-dihydro-1-methyl-7-oxo-3-propyl-1H-pyrazolo(4,3-d)pyrimidin-5-yl)-(4-ethoxyphenyl)benzene sulfonyl chloride (100 g, 0.24 mol) was mixed with acetone (1000 ml) at room temperature and NaOH (9.74 g, 47%). N-methyl piperazine (26.8 g, 0.27 mol) was added dropwise. The reaction mixture was stirred for 45 mm, cooled to 0° C., and filtered. The collected precipitate was washed with water twice and dried at 50° C. under 10 mm Hg to yield pure sildenafil in 85% yield.

Example 25

Preparation of Sildenafil

In a 3-necked flask, N-methyl piperazine (1.34 g, 13.4 mol) and NaOH (47%, 0.49 g) were mixed at room temperature. 3-(4,7-dihydro-1-methyl-7-oxo-3-propyl-1H-pyrazolo(4,3-d)pyrimidin-5-yl)-(4-ethoxyphenyl)benzene sulfonyl chloride (5 g, 12.2 mmol) was suspended in acetone (50 ml) and the suspension was added to the mixture of bases to form a reaction mixture. The reaction mixture was stirred for 45 mm, cooled to 0° C., and filtered. The collected precipitate was washed with water twice and dried at 50° C. under 10 mm Hg to yield pure sildenafil in 87% yield.

Example 26

Preparation of Sildenafil

In a 3-necked flask, N-methyl piperazine (1.34 g, 13.4 mmol) and 3-(4,7-dihydro-1-methyl-7-oxo-3-propyl-1H-pyrazolo(43-d)pyrimidin-5-yl)-(4-ethoxyphenyl)benzene sulfonyl chloride (5 g) were suspended in acetone (50 ml) at room temperature. NaOH (0.49 g, 47%) was added dropwise. The reaction mixture was stirred for 45 mm, cooled to 0° C., and filtered. The collected precipitate was washed with water twice and dried at 50° C. under 10 mm Hg to give pure sildenafil in 86.3% yield.

Example 27

Preparation of Sildenafil Citrate

In a 3-necked flask, 3-(4,7-dihydro-1-methyl-7-oxo-3-propyl-1H-pyrazolo(4,3-d)pyrimidin-5-yl)-(4-ethoxyphenyl)benzene sulfonyl chloride (10 g, 0.024 mol) was mixed with acetone (100 ml) and NaOH (0.974 g, 47%) at room temperature. N-methyl piperazine (2.68 g, 0.027 mol) was added dropwise to the mixture. Thereafter, the reaction was stirred for 45 mm, additional acetone (100 ml) was added, and then the mixture was heated to reflux. Citric acid (5 g, 0.024 mol) was added, and a white precipitate appeared immediately. The reaction was maintained at reflux for one hour and then allowed to cool to room temperature over 3 hours. The precipitate was collected by filtration, and dried at 50° C. under 10 mm Hg to give pure sildenafil citrate in 72% yield.

Example 28

Preparation of Sildenafil Citrate

In a 3-necked flask, sildenafil (5 g, 10 mmol) was dissolved in acetone (100 ml) at reflux. Citric acid (2 g, 10 mmol) was added, and a white precipitate appeared immediately. The reaction mixture was maintained at the reflux temperature for 1 hour and allowed to cool over 3 hours to room temperature. The precipitate was collected, filtered, and dried at 50° C. under 10 mm Hg to give pure sildenafil citrate in 94% yield.

Example 29

Preparation of Sildenafil Citrate

In a 3-necked flask, sildenafil (5 g, 10 mmol) and citric acid (2 g, 10 mmol) were suspended in acetone (100 ml). The reaction mixture was heated to reflux and maintained at reflux for 1 hour, thereafter, the reaction mixture was allowed to cool for 3 hours to room temperature. The precipitate was collected by filtration and dried at 50° C. under 10 mm Hg to give pure sildenafil citrate in 94.4% yield.

Example 30

Drying Procedures I

Sildenafil citrate was dried in an oven at 50° C., using a high vacuum pump (2 mm Hg) for 17 hours, until the weight of the solid was constant. The water content measured by Karl Fischer method showed a content of 1.7%.

Example 31

Drying Procedures II

Sildenafil citrate was dried in an oven at 80° C., using a high vacuum pump (2 mm Hg) for 12 hours until the weight of the solid was constant. The water content measured by Karl Fischer method showed a content of 1.5%.

Example 32

Drying Procedures III

Sildenafil citrate from Example 30 was dried in an oven at 100° C., using a high vacuum pump (2 mm Hg) for 17 hours. The water content measured by Karl Fischer method showed a content of 0.3%. After standing open overnight, the water content increased to 1.2%.

Example 33

Surface Area Measurement of Sildenafil Citrate

The sildenafil citrate adducts were measured using a Coulter SA3100 instrument and a sample cell of 9 cc. No degassing took place, but the sensitivity was set for high, the calculation for BET, and type at multipoint to collect 10 points.

Example 34

Preparation of Sildenafil Citrate

In a 0.25 L reactor equipped with mechanical stirrer and thermometer, 100 ml of acetone was added. The reactor was maintained at room temperature (22° C.). 5.35 g of N-methyl piperazine (1.1 equivalents) followed by 4.16 g of NaOH solution (47%, 1 equivalent) were added. 20 g of 1-[[3-(4,7-Dihydro-1-methyl-7-oxo-3-propyl-1H-pyrazolo[4,3-d]pyrimidin-5-yl)-4-ethoxyphenyl] sulfonyl chloride was added portion-wise (5 g each). The reaction mixture was kept at room temperature with mixing for 1 hour. The reaction mixture was kept at 5° C. for 2 hours. During that period, sildenafil base precipitated. After filtration, the cake was washed with water (50 ml). 29.24 g wet sildenafil base was obtained.

In a 0.5 L reactor equipped with mechanical stirrer and thermometer, 27 g wet sildenafil base and 100 ml water were added. The reaction mixture was maintained at 25° C. with mixing for 1 hour and filtered. 23.5 g wet sildenafil base was obtained. (Yield 91%)

In a 0.5 L reactor equipped with mechanical stirrer, 370 ml acetone and 21.4 g wet sildenafil base were added. The mixture was heated to reflux. In a separate vessel, 8.95 g of citric acid was dissolved in 89.5 ml of acetone at room temperature.

The solution was added dropwise. Upon completion of the addition, the reaction mixture was maintained at reflux for 1 hour, followed by 2 hours at room temperature. Sildenafil citrate precipitated during this period was filtered, and the cake was washed with acetone. 28.1 g wet sildenafil citrate was obtained and dried for 4 hours at 50° C. 25.5 g sildenafil citrate dry was obtained. (Yield of this step: 98.8%).

The overall yield was 83.3%.

Example 35

Micronization to Particle Size d(0.9)<20 microns

A fluid-energy mill, (model: Micro-Grinding 100 mm) was used. The sample was fed into the micronizer by a screw feeder. The feed air pressure was between 4 bar and the grinding air pressure 3 bar. The feed rate was 2.4 kg/hr.

Example 36

Micronization to Particle Size d(0.9)=86 microns

A cone-mill was used (model: Quadro-comil 197). The screen size was ~500 microns opening diameter and the mill speed was 6000 rpm.

Example 37

Micronization to Particle Size d(0.9)=128 microns

A cone-mill was used (model: Quadro-comil 197). The screen size was ~500 microns opening diameter and the mill speed was 3000 rpm.

What is claimed is:

1. A process for preparing sildenafil comprising combining 3-(4,7-dihydro-1-methyl-7-oxo-3-propyl-1H-pyrazolo(4,3-d)pyrimidin-5-yl)-(4-ethoxyphenyl)benzene sulfonyl chloride with at most about 1 molar equivalent of N-methyl piperazine, at least one organic solvent, and at least one proton scavenger into a reaction mixture to form sildenafil; wherein the proton scavenger is an inorganic base.

2. The process of claim 1, wherein the N-methyl piperazine is present in an amount of about 1 molar equivalent of the 3-(4,7-dihydro-1-methyl-7-oxo-3-propyl-1H-pyrazolo(4,3-d)pyrimidin-5-yl)-(4-ethoxyphenyl)benzene sulfonyl chloride.

3. The process of claim 1, wherein the organic solvent is at least one of acetone, isopropanol, ethanol, methanol, acetonitrile, ethyl acetate, methyl ethyl ketone, dichloromethane, or toluene.

4. The process of claim 3, wherein the organic solvent is at least one of acetone, ethanol, or methanol.

5. The process of claim 1, wherein the proton scavenger is at least one of NaOH, KOH, $NaHCO_3$, $KHCO_3$, $Na_2CO_3$, $K_2CO_3$, or $Ca(OH)_2$.

6. The process of claim 1, wherein the proton scavenger is present in an amount of from about 0.8 mol to about 1.5 mol per mol of the 3-(4,7-dihydro-1-methyl-7-oxo-3-propyl-1H-pyrazolo(4,3-d)pyrimidin-5-yl)-(4-ethoxyphenyl)benzene sulfonyl chloride.

7. The process of claim 6, wherein the proton scavenger is present in an amount of about 1 mol per mol of the 3-(4,7-dihydro-1-methyl-7-oxo-3-propyl-1H-pyrazolo(4,3-d)pyrimidin-5-yl)-(4-ethoxyphenyl)benzene sulfonyl chloride.

8. The process of claim 1, wherein the reaction mixture is maintained at a temperature of from about 0° C. to about reflux temperature.

9. The process of claim 1, further comprising combining water with the reaction mixture.

10. The process of claim 1, wherein combining the 3-(4,7-dihydro-1-methyl-7-oxo-3-propyl-1H-pyrazolo(4,3-d)pyrimidin-5-yl)-(4-ethoxyphenyl)benzene sulfonyl chloride with the N-methyl piperazine, the organic solvent, and the proton scavenger is carried out by adding the 3-(4,7-di-hydro-1-methyl-7-oxo-3-propyl-1H-pyrazolo(4,3-d)pyrimidin-5-yl)-(4-ethoxyphenyl)benzene sulfonyl chloride to a mixture of the N-methyl piperazine, the organic solvent and the proton scavenger.

11. A process for preparing sildenafil citrate comprising
  (a) combining 3-(4,7-dihydro-1-methyl-7-oxo-3-propyl-1H-pyrazolo(4,3-d)pyrimidin-5-yl)-(4-ethoxyphenyl) benzene sulfonyl chloride with at most about 1 molar equivalent of N-methyl piperazine, at least one organic solvent, and at least one proton scavenger into a reaction mixture to form sildenafil; and
  (b) combining the thus prepared sildenafil with citric acid into a reaction mixture to form sildenafil citrate;
  wherein the proton scavenger is an inorganic base.

12. The process of claim 11, wherein the reaction mixture in step (b) further comprises at least one organic solvent.

13. The process of claim 12 wherein the organic solvent in step (a) is at least one of acetone, acetonitrile, methanol, ethanol, isopropanol, ethyl acetate, isobutyl acetate, butyl acetate, methyl acetate, toluene, heptane, or methylene chloride.

14. The process of claim 13, wherein the organic solvent in step (a) is acetone.

15. The process of claim 11, wherein the citric acid is present in an amount of from about 1 molar equivalent to about 2 molar equivalents of the sildenafil.

16. The process of claim 11, wherein the reaction mixture is maintained at a temperature of from about 0° C. to about 130° C.

17. The process of claim 16, wherein the reaction mixture is maintained at reflux temperature.

18. Sildenafil citrate water adduct comprising water in the amount of from about 1.5% to about 1.7% by weight, wherein the sildenafil citrate water adduct has a particle size of less than about 100 microns.

19. The sildenafil citrate water adduct of claim 18 having a particle size of less than about 50 microns.

20. The sildenafil citrate water adduct of claim 19 having a particle size of less than about 20 microns.

21. Sildenafil citrate water adduct comprising water in the amount of from about 1.5% to about 1.7% by weight, wherein the sildenafil citrate water adduct particles have a surface area of from about 4 $m^2/g$ to about 6 $m^2/g$.

22. The sildenafil citrate water adduct of claim 21 having a surface area of about 5 $m^2/g$.

23. Sildenafil citrate water adduct comprising water in the amount of from about 1.5% to about 1.7% by weight and a melting point in the range of from about 185° C. to about 193° C.

24. The sildenafil citrate water adduct of claim 23 having a melting point in the range of from about 188° C. to about 192° C.

25. The sildenafil citrate water adduct of claim 23 having a melting point in the range of from about 188° C. to about 192° C.

26. Sildenafil citrate having a melting point in the range of from about 185° C. to about 190° C.

27. A method of preparing a pharmaceutical composition comprising combining the sildenafil citrate of any one of claims 18, 21, 23 and 26 with at least one pharmaceutically-acceptable excipient.

28. A process for preparing sildenafil citrate comprising
a) combining 3-(4,7-dihydro-1-methyl-7-oxo-3-propyl-1H-pyrazolo(4,3-d)pyrimidin-5-yl)-(4-ethoxyphenyl) benzene sulfonyl chloride with at most about 1 molar equivalent of N-methyl piperazine, at least one organic solvent, and at least one proton scavenger into a reaction mixture;
b) maintaining the reaction mixture at a temperature of from about 0° C. to about reflux temperature for up to about 24 hours; and
c) adding citric acid into a reaction mixture to form sildenafil citrate.

* * * * *

UNITED STATES PATENT AND TRADEMARK OFFICE
CERTIFICATE OF CORRECTION

PATENT NO. : 7,618,976 B2
APPLICATION NO. : 11/030545
DATED : November 17, 2009
INVENTOR(S) : Braude et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Twenty-sixth Day of October, 2010

David J. Kappos
*Director of the United States Patent and Trademark Office*